(12) United States Patent
Takasu (10) Patent No.: US 8,173,069 B2
(45) Date of Patent: May 8, 2012

(54) ION ANALYZING APPARATUS AND ION ANALYZING METHOD

(75) Inventor: Ryozo Takasu, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/227,596

(22) Filed: Sep. 8, 2011

(65) Prior Publication Data

US 2011/0316550 A1 Dec. 29, 2011

Related U.S. Application Data

(62) Division of application No. 12/856,142, filed on Aug. 13, 2010, now Pat. No. 8,034,295.

(30) Foreign Application Priority Data

Aug. 18, 2009 (JP) ................... 2009-188862

(51) Int. Cl.
*G01N 33/00* (2006.01)
*G01N 33/48* (2006.01)
*G01N 15/06* (2006.01)

(52) U.S. Cl. ... 422/68.1; 422/50; 422/82.01; 422/82.02; 422/82.03; 436/43

(58) Field of Classification Search .................... 422/50, 422/68.1, 82.01, 82.02, 82.03; 436/43
See application file for complete search history.

(56) References Cited

U.S. PATENT DOCUMENTS

| 3,794,575 A | 2/1974 | Niedrach et al. |
| 4,609,454 A | 9/1986 | Ziegler |
| 2008/0179998 A1 | 7/2008 | Kawashima |
| 2009/0015263 A1* | 1/2009 | Nakajima ............... 324/457 |
| 2009/0178923 A1 | 7/2009 | Marquant et al. |
| 2009/0178936 A1 | 7/2009 | Zhu |

FOREIGN PATENT DOCUMENTS

| JP | 60-221776 A | 11/1985 |
| JP | 5-036490 A | 2/1993 |
| JP | 2007-147495 A | 6/2007 |
| JP | 2009-098084 A | 5/2009 |
| JP | 2009-150747 A | 7/2009 |

OTHER PUBLICATIONS

USPTO, [SINES] "U.S. Appl. No. 12/856,142 (parent)," [CTNF] Non-Final Office Action issued on Apr. 7, 2011.
USPTO, [SINES] "U.S. Appl. No. 12/856,142 (parent)," [CTRS] Requirement for Restriction/Election issued on Mar. 1, 2011.
USPTO, [SINES] "U.S. Appl. No. 12/856,142 (parent)," [NOA] Notice of Allowance and Fees Due issued on Aug. 8, 2011.

* cited by examiner

*Primary Examiner* — Brian J Sines
(74) *Attorney, Agent, or Firm* — Fujitsu Patent Center (57) ABSTRACT

An ion analyzing apparatus includes a sensor; a counter electrode having openings, the counter electrode being positioned so as to substantially surround the sensor; and a bias generating circuit coupled to the sensor, wherein the sensor includes quartz crystal and a pair of electrodes positioned on surface of the quartz crystal, and one of the pair of electrodes is coupled to the bias generating circuit.

5 Claims, 11 Drawing Sheets

ION ANALYZING APPARATUS AND ION ANALYZING METHOD

CROSS-REFERENCE TO RELATED APPLICATION(S)

This application is based upon and claims the benefit of priority of the prior Japanese Patent Application No. 2009-188862, filed on Aug. 18, 2009, the entire contents of which are incorporated herein by reference.

FIELD

The embodiment discussed herein relates to an ion analyzing apparatus and ion analyzing method.

BACKGROUND

In manufacturing of electronic devices such as semiconductor devices, static electricity generated in the electronic devices and/or manufacturing apparatuses may affect the performance of the devices and/or the manufacturing yields. Therefore, ionizers are widely used at the manufacturing sites of electronic devices in order to remove static electricity.

An ionizer has a needle-type electrode. For example, corona discharge occurs at the tip of the electrode upon application of a high voltage of a few kilovolts of electricity to the electrode, and air ions are generated at the tip of the electrode. Using a fan blower, for example, the generated air ions are sprayed over an electrically charged target to be discharged, thereby neutralizing the electric charge of the target to be discharged. In this manner, static electricity of the target to be discharged may be removed.

SUMMARY

According to an aspect of an embodiment, an ion analyzing apparatus includes a sensor; a counter electrode having openings, the counter electrode being positioned so as to substantially surround the sensor; and a bias generating circuit coupled to the sensor, wherein the sensor includes quartz crystal and a pair of electrodes positioned on surface of the quartz crystal, and one of the pair of electrodes is coupled to the bias generating circuit.

According to another aspect of an embodiment, an ion analyzing method includes measuring a change in a first oscillation frequency of a sensor in time; measuring a change in a second oscillation frequency of the sensor in time while applying a bias voltage to the sensor and allowing ions that pass through openings provided in a counter electrode positioned so as to substantially surround the sensor to be adsorbed on the sensor; and detecting adsorption of the ions on the sensor from a difference between the change in the first oscillation frequency in time and the change in the second oscillation frequency in time.

The object and advantages of the invention will be realized and attained by at least those elements, features, and combinations particularly pointed out in the claims.

It is to be understood that both the foregoing general description and the following detailed description are exemplary and explanatory and are not restrictive of the invention, as claimed.

DESCRIPTION OF EMBODIMENTS

A first embodiment will be described with reference to FIGS. 1 to 4.

Figure 1:
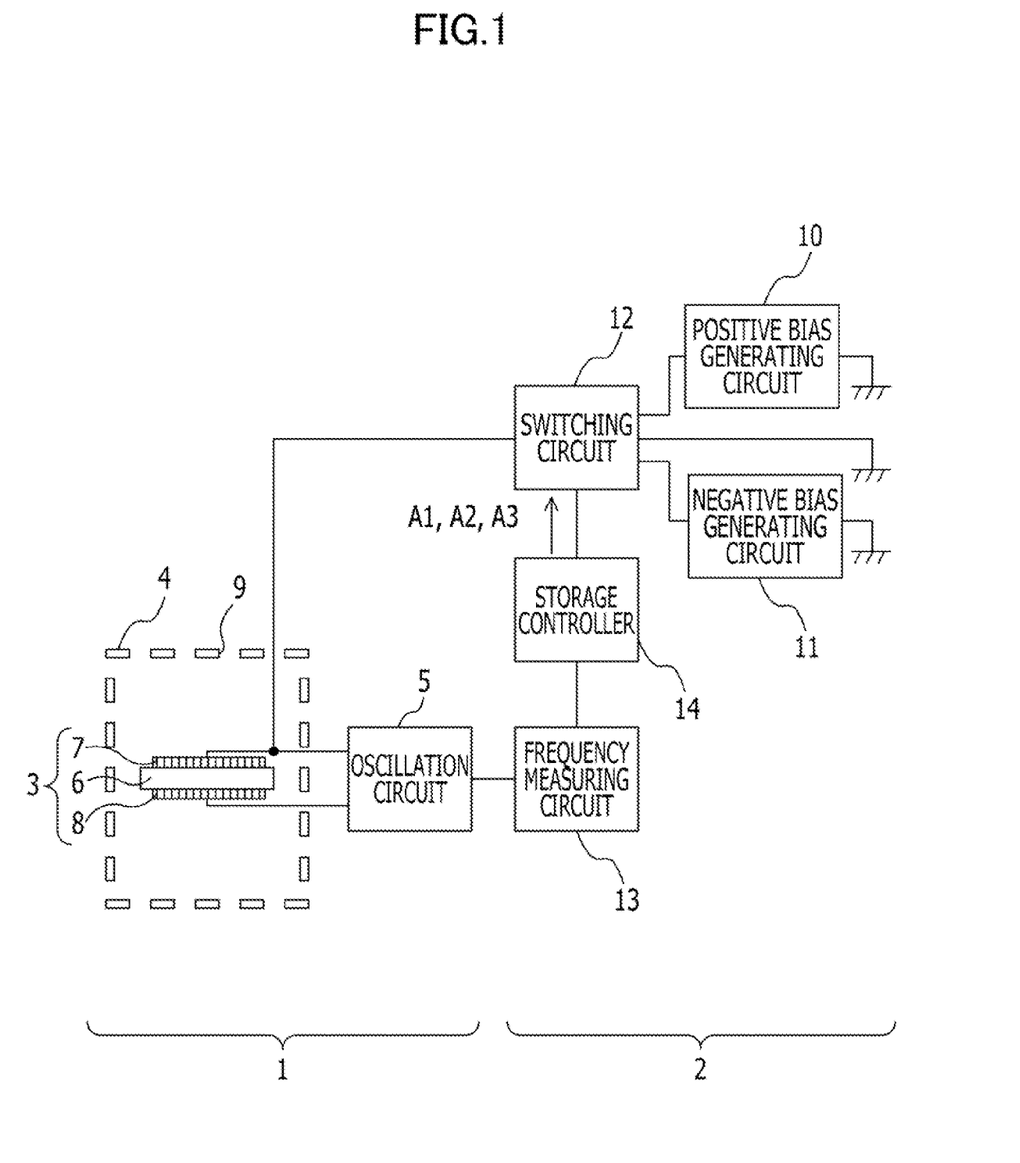
FIG. 1 is a diagram illustrating an exemplary ion analyzing apparatus according to a first embodiment.

FIG. 1 is a diagram illustrating an ion analyzing apparatus according to a first embodiment. As illustrated in FIG. 1, the ion analyzing apparatus includes a sensor unit 1 and a control unit 2.

Each unit of the ion analyzing apparatus will now be described in more detail.

The sensor unit 1 includes a sensor 3, a counter electrode 4, and an oscillation circuit 5.

The sensor 3 includes, for example, a quartz crystal oscillator including a pair of electrodes 7 and 8 on surfaces of quartz crystal 6. An oscillation circuit 5 configured to apply a voltage to the electrodes 7 and 8 is coupled to the electrodes 7 and 8.

The sensor 3 is called a micro balance sensor or a quartz crystal oscillator microbalance (QCM) sensor, for example. A QCM sensor uses the phenomenon in which the oscillation frequency of the quartz crystal oscillator changes in accordance with the mass of the quartz crystal oscillator. A QCM sensor detects the presence of a matter based on a change in the oscillation frequency of the quartz crystal oscillator when the matter in the atmosphere is adsorbed on the surface of the quartz crystal oscillator.

For example, a change $\Delta F$[Hz] in the oscillation frequency may be expressed by:

$$\Delta F = -F0^2 \cdot \Delta m / (N \cdot \rho \cdot A)$$

where F0 [MHz] indicates the basic frequency when there is no adsorption, N [Hz·cm] indicates the frequency constant of the quartz crystal used, A [cm$^2$] indicates the area of the electrodes, $\rho$ [g·cm$^{-3}$] indicates the density of the quartz crystal used, and $\Delta m$ [g] indicates the mass of the adsorbed matter. Since the oscillation frequency changes by $\Delta F$ because of the mass $\Delta m$ of the adsorbed matter, the amount of the adsorbed matter may be measured by measuring $\Delta F$.

ΔF of 1 Hz corresponds to an adsorbed amount of about 1 ng·cm$^{-2}$ when a quartz crystal oscillator with F0 of 25 MHz is used. Adsorption of a subnanogram/cm$^2$ may be detected by using the QCM sensor.

The counter electrode 4 is positioned so as to substantially surround the sensor 3 and includes a plurality of openings 9. A conductive and oxidation-resistant material is preferable as the material of the counter electrode 4, and metal such as stainless steel or nickel (Ni) may be used. The gap between the sensor 3 and the counter electrode 4 is, for example, about 3 mm to 10 mm.

Positioning the counter electrode 4 so as to substantially surround the sensor 3 allows the counter electrode 4 to have a shielding effect against an electric field generated between the sensor 3 and the counter electrode 4. Therefore, an electric field is prevented from leaking out of the counter electrode 4, thus avoiding a change in the distribution of ions.

The use of the counter electrode 4 with the openings 9 allows adsorption of ions outside the counter electrode 4, through the openings 9, onto the sensor 3, as described later. In order to increase the ease of passage of ions, a higher aperture ratio of a mesh is more preferable. However, the higher the aperture ratio, the weaker the shielding effect. This results in a higher probability of leakage of the electric field. To avoid such a problem, the counter electrode 4 preferably has a mesh shape. For example, the aperture ratio is preferably about 90%, and the pitch of the mesh is preferably about 60 mesh.

Figure 2A:
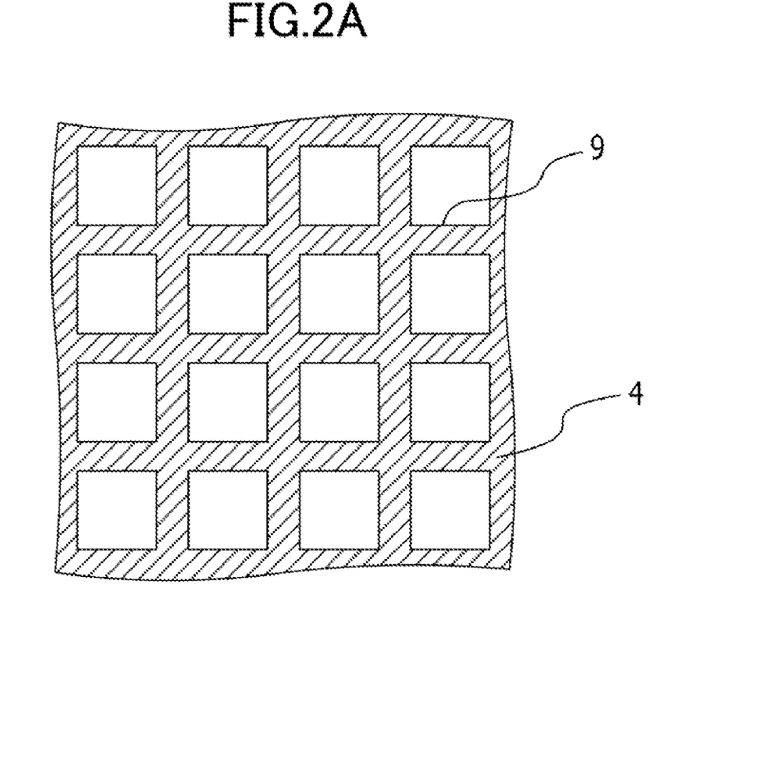
FIGS. 2A and 2B are plan views illustrating examples of a counter electrode in the first embodiment.
Figure 2B:
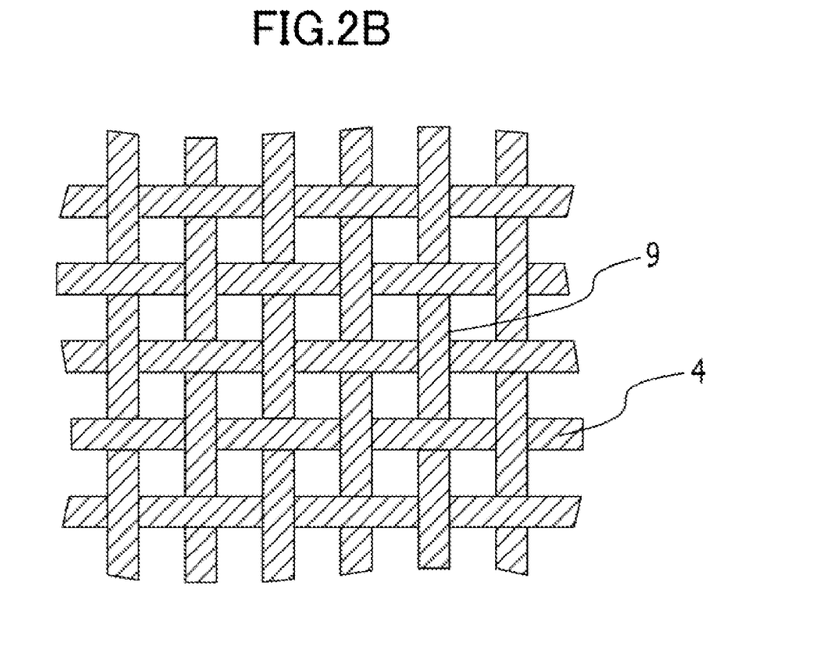

FIGS. 2A and 2B are plan views illustrating examples of the counter electrode 4. As illustrated in FIG. 2A, a material with the plurality of openings 9 may be used as the counter electrode 4. Alternatively, as illustrated in FIG. 2B, a cloth-type material shaped as a grid (or ribbons) may be used as the counter electrode 4 with the openings 9. The thickness of the counter electrode 4 is, for example, about 400 μm.

With the use of the mesh-type counter electrode 4, the counter electrode 4 with a desired aperture ratio may be easily manufactured, and the thickness of the counter electrode 4 may be reduced.

Referring back to FIG. 1, the oscillation circuit 5 is coupled to the pair of electrodes 7 and 8 of the sensor 3, and the oscillation circuit 5 may apply a voltage to the electrodes 7 and 8. The absolute value of the magnitude of the voltage is, for example, about 5 V.

The control unit 2 includes a positive bias generating circuit 10, a negative bias generating circuit 11, a switching circuit 12, a frequency measuring circuit 13, and a storage controller 14.

The positive bias generating circuit 10 and the negative bias generating circuit 11 are coupled to the electrode 7 of the sensor 3 via the common switching circuit 12, and the positive bias generating circuit 10 and the negative bias generating circuit 11 may apply a positive bias or a negative bias to the electrode 7. The absolute value of the positive bias or the negative bias is, for example, about 100 V. The oscillation circuit 5 is coupled to the frequency measuring circuit 13. The frequency measuring circuit 13 measures a change ΔF in the frequency of the oscillation circuit 5.

The frequency measuring circuit 13 is coupled to the storage controller 14. The value of change ΔF in frequency, which is measured by the frequency measuring circuit 13, may be stored in the storage controller 14.

The storage controller 14 also performs switching control of the connection between the electrode 7 of the sensor 3 and the positive bias generating circuit 10 or the negative bias generating circuit 11 by driving the switching circuit 12. For example, a personal computer (PC) may be used as the storage controller 14.

Figure 3:
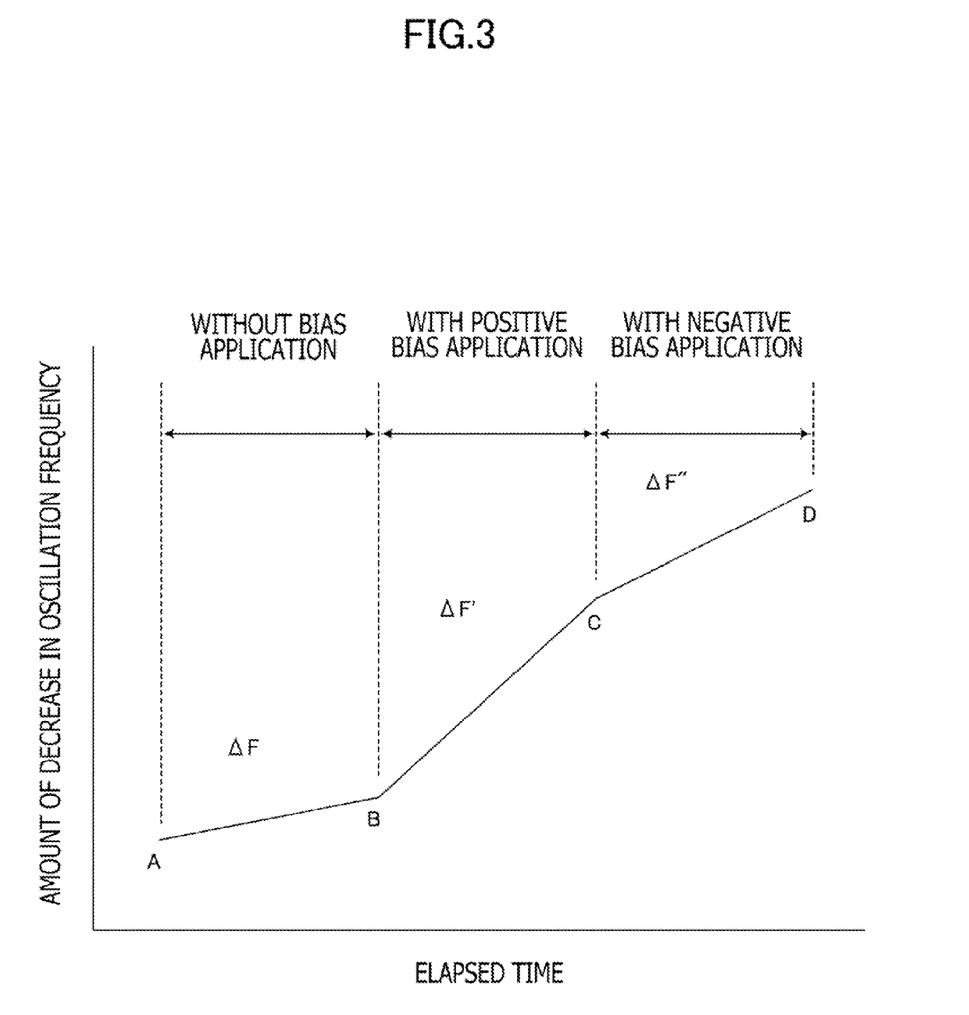
FIG. 3 is a graph illustrating an example of an analyzing method using the ion analyzing apparatus according to the first embodiment.

FIG. 3 is a graph illustrating an analyzing method using the ion analyzing apparatus according to the first embodiment. The method is described in conjunction with FIG. 1.

Firstly, the storage controller 14 sends a control signal A1 to the switching circuit 12. After the switching circuit 12 receives the control signal A1, a change ΔF in the oscillation frequency is measured without application of a voltage to the sensor 3 from elapsed time A to B, such as for ten minutes.

Since matter existing in the atmosphere moves by diffusion, the matter reaches the sensor 3 and is adsorbed on the sensor 3 without application of a voltage to the sensor 3. With the adsorption, the mass of the sensor 3 increases by Δm, and the oscillation frequency decreases by ΔF. Gradients in FIG. 3 are values that reflect the amount of adsorption per unit time.

Then, the storage controller 14 sends a control signal A2 to the switching circuit 12. After the switching circuit 12 receives the control signal A2, a change ΔF' in the frequency is measured with application of a positive bias to the sensor 3 from elapsed time B to C, such as for ten minutes. Since the sensor 3 is charged positively upon application of the positive bias to the sensor 3, negative ions are adsorbed on the sensor 3.

Since the counter electrode 4 includes the openings 9, negative ions outside the counter electrode 4 may pass through the openings 9 and reach the sensor 3, which is positioned inside the counter electrode 4. The counter electrode 4 is preferably grounded from a viewpoint of preventing adsorption of ions on the counter electrode 4.

Matter adsorbed on the sensor 3 as a result of application of the positive bias includes matter with electric charge and matter without electric charge. The effects of the matter without electric charge may be removed by subtracting ΔF, which is measured without application of a voltage, from ΔF', which is measured with application of the positive bias. The gradient of the difference between ΔF, which is measured without application of a voltage, and ΔF', which is measured with application of the positive bias, is a value that reflects the density of the negative ions.

Then, the storage controller 14 sends a control signal A3 to the switching circuit 12. After the switching circuit 12 receives the control signal A3, a change ΔF'' in the frequency is measured with application of a negative bias to the sensor 3 from elapsed time C to D, such as for ten minutes. Since the sensor 3 is charged negatively upon application of the negative potential to the sensor 3, positive ions are adsorbed on the sensor 3.

Positive ions outside the counter electrode 4 may also pass through the openings 9 and reach the sensor 3, which is positioned inside the counter electrode 4.

Matter adsorbed on the sensor 3 as a result of application of the negative bias includes matter with electric charge and matter without electric charge. The effects of the matter without electric charge may be removed by subtracting ΔF, which is measured without application of a voltage, from ΔF'', which is measured with application of the negative bias. The gradient of the difference between ΔF, which is measured without application of a voltage, and ΔF'', which is measured with application of the negative bias, is a value that reflects the density of the positive ions.

With a comparison of ΔF', which is measured using the foregoing method with application of the positive bias, and ΔF'', which is measured using the foregoing method with application of the negative bias, the positive-negative balance of ions in the space where the measurements have been done may be detected, and an ionizer's effect of discharging a target to be discharged may be detected. Changes in the ion densities in time may be substantially constantly measured (monitored) by repeating the foregoing procedure.

Figure 4:
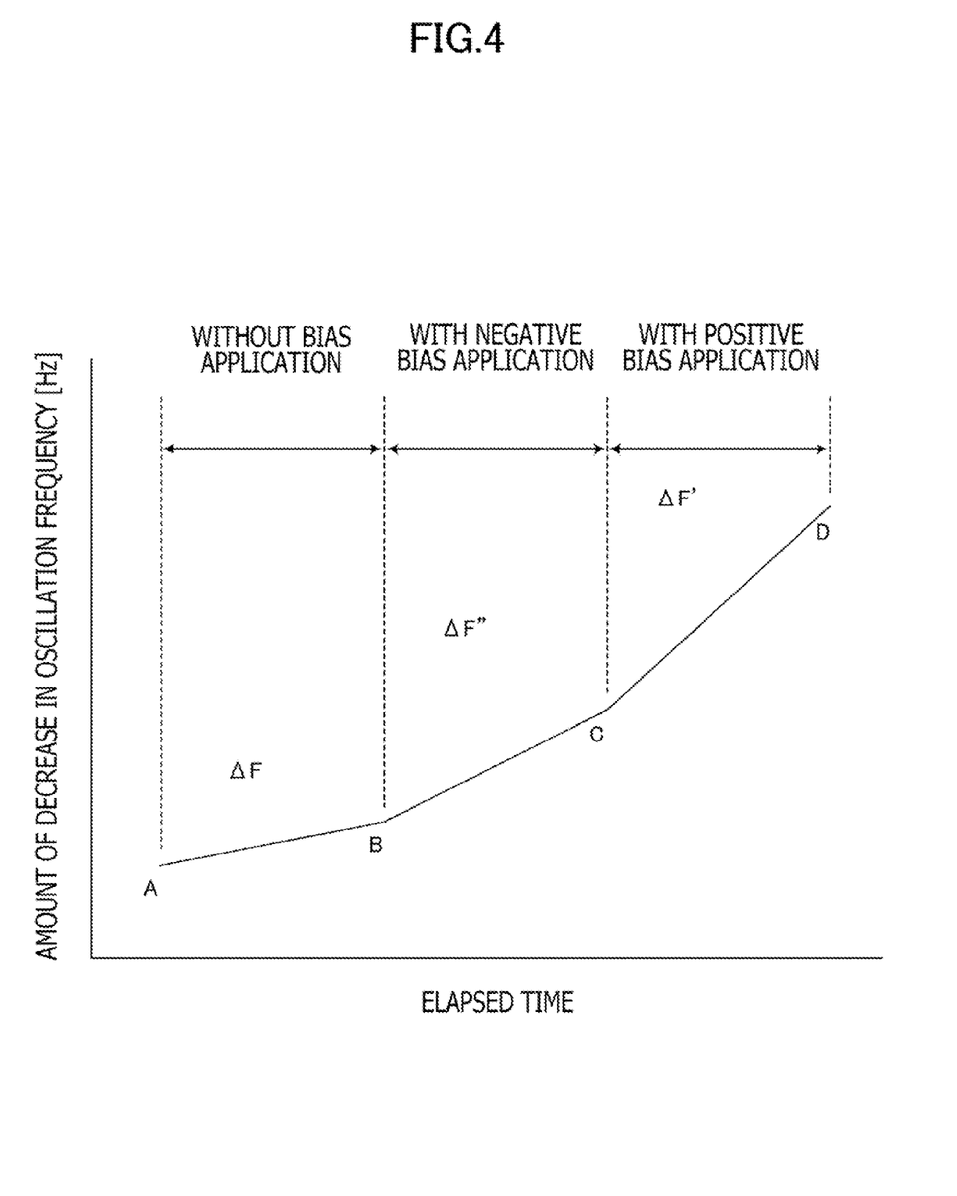
FIG. 4 is a graph illustrating another example of the analyzing method using the ion analyzing apparatus according to the first embodiment.

FIG. 4 is a graph illustrating another example of the analyzing method using the ion analyzing apparatus according to the first embodiment.

Firstly, as illustrated in FIG. 3 of the first embodiment, the storage controller 14 sends the control signal A1 to the switching circuit 12. A change in ΔF in the oscillation frequency is measured without application of a voltage to the sensor 3 from elapsed time A to B, such as for ten minutes.

Then, the storage controller 14 sends the control signal A3 to the switching circuit 12. After the switching circuit 12 receives the control signal A3, a change in ΔF" in the frequency is measured with application of a negative bias to the sensor 3 from elapsed time B to C, such as for ten minutes. Since the sensor 3 is charged negatively upon application of the negative bias to the sensor 3, positive ions are adsorbed on the sensor 3. The gradient of a difference obtained by subtracting ΔF, which is measured without application of a voltage, from ΔF", which is measured with application of the negative bias, is a value that reflects the density of the positive ions serving as a target to be measured.

Then, the storage controller 14 sends the control signal A2 to the switching circuit 12. After the switching circuit 12 receives the control signal A2, a change in ΔF' in the frequency is measured with application of a positive bias to the sensor 3 from elapsed time C to D, such as for ten minutes. Since the sensor 3 is charged positively upon application of the positive bias to the sensor 3, negative ions are adsorbed on the sensor 3. The gradient of a difference obtained by subtracting ΔF, which is measured without application of a voltage, from ΔF', which is measured with application of the positive bias, is a value that reflects the density of the negative ions serving as a target to be measured.

With a comparison of ΔF', which is measured using the foregoing method with application of the positive bias, and ΔF", which is measured using the foregoing method with application of the negative bias, the positive-negative balance of ions in the space where the measurements have been done may be detected, and an ionizer's effect of discharging a target to be discharged may be detected.

A second embodiment will now be described with reference to FIGS. 5 to 9.

Figure 5:
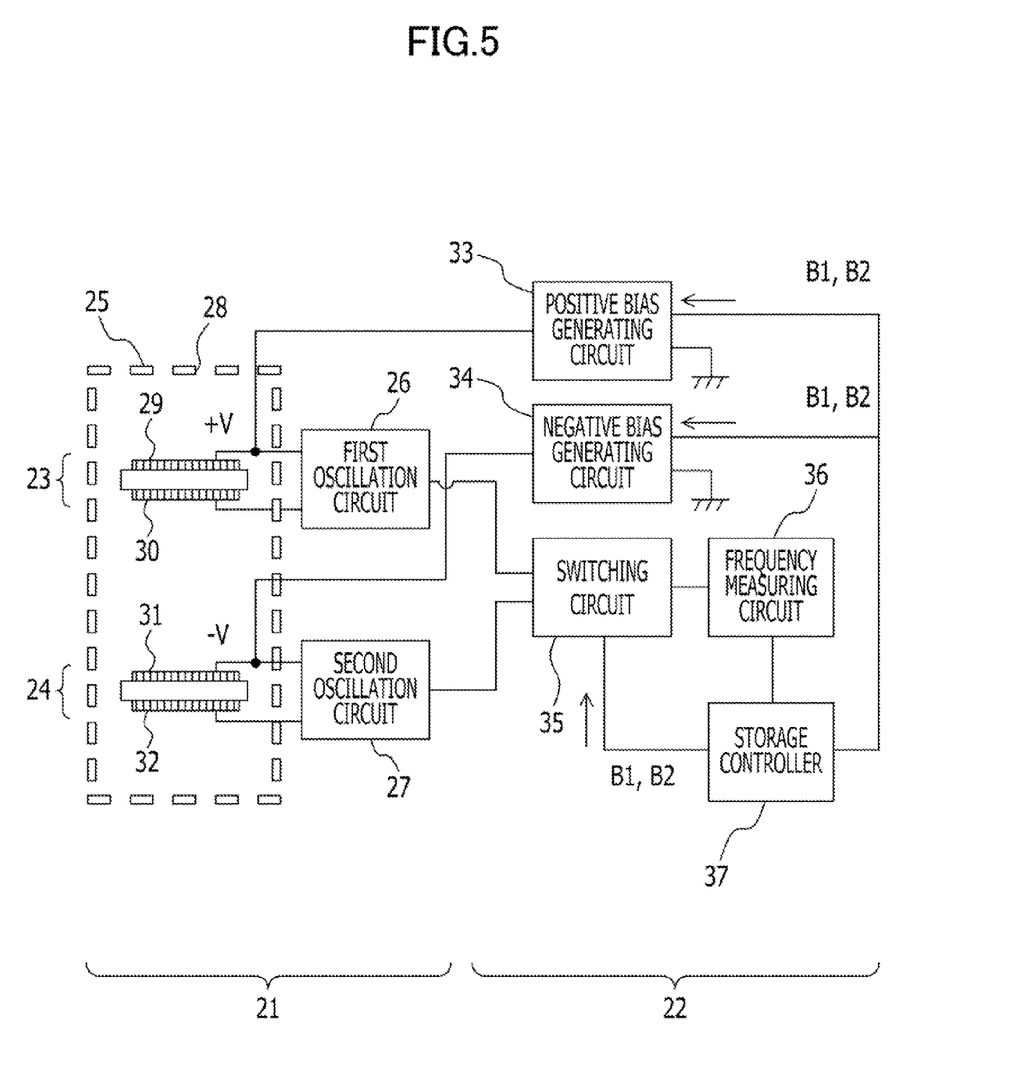
FIG. 5 is a diagram illustrating an exemplary ion analyzing apparatus according to a second embodiment.

FIG. 5 is a diagram illustrating an ion analyzing apparatus according to the second embodiment.

The ion analyzing apparatus includes a sensor unit 21 and a control unit 22.

Each unit of the ion analyzing apparatus will now be described in more detail.

The sensor unit 21 includes a first sensor 23, a second sensor 24, a counter electrode 25, a first oscillation circuit 26, and a second oscillation circuit 27.

The first sensor 23 and the second sensor 24 may be substantially surrounded by the counter electrode 25 having openings 28. The gap between the first sensor 23 and the second sensor 24 is, for example, about 6 mm to 20 mm. The first oscillation circuit 26 is coupled to electrodes 29 and 30 of the first sensor 23. The second oscillation circuit 27 is coupled to electrodes 31 and 32 of the second sensor 24.

The control unit 22 includes a positive bias generating circuit 33, a negative bias generating circuit 34, a switching circuit 35, a frequency measuring circuit 36, and a storage controller 37.

The positive bias generating circuit 33 is coupled to the electrode 29 of the first sensor 23, and the positive bias generating circuit 33 may apply a positive bias to the electrode 29. The negative bias generating circuit 34 is coupled to the electrode 31 of the second sensor 24, and the negative bias generating circuit 34 may apply a negative bias to the electrode 31.

The first oscillation circuit 26 and the second oscillation circuit 27 are coupled via the switching circuit 35 to the frequency measuring circuit 36.

The frequency measuring circuit 36 is coupled to the storage controller 37. Values of changes ΔF1 and ΔF2 in the frequencies of the first oscillation circuit 26 and the second oscillation circuit 27, respectively, which are measured by the frequency measuring circuit 36, may be stored in the storage controller 37. The storage controller 37 may also perform control for applying a positive or negative bias voltage to the first sensor 23 or the second sensor 24 by driving the positive bias generating circuit 33 or the negative bias generating circuit 34.

The storage controller 37 may perform control for switching connection between the frequency measuring circuit 36 and the first oscillation circuit 26 or the second oscillation circuit 27, which serves as a target whose change in the frequency is to be measured, by driving the switching circuit 35. For example, a PC may be used as the storage controller 37.

Figure 6:
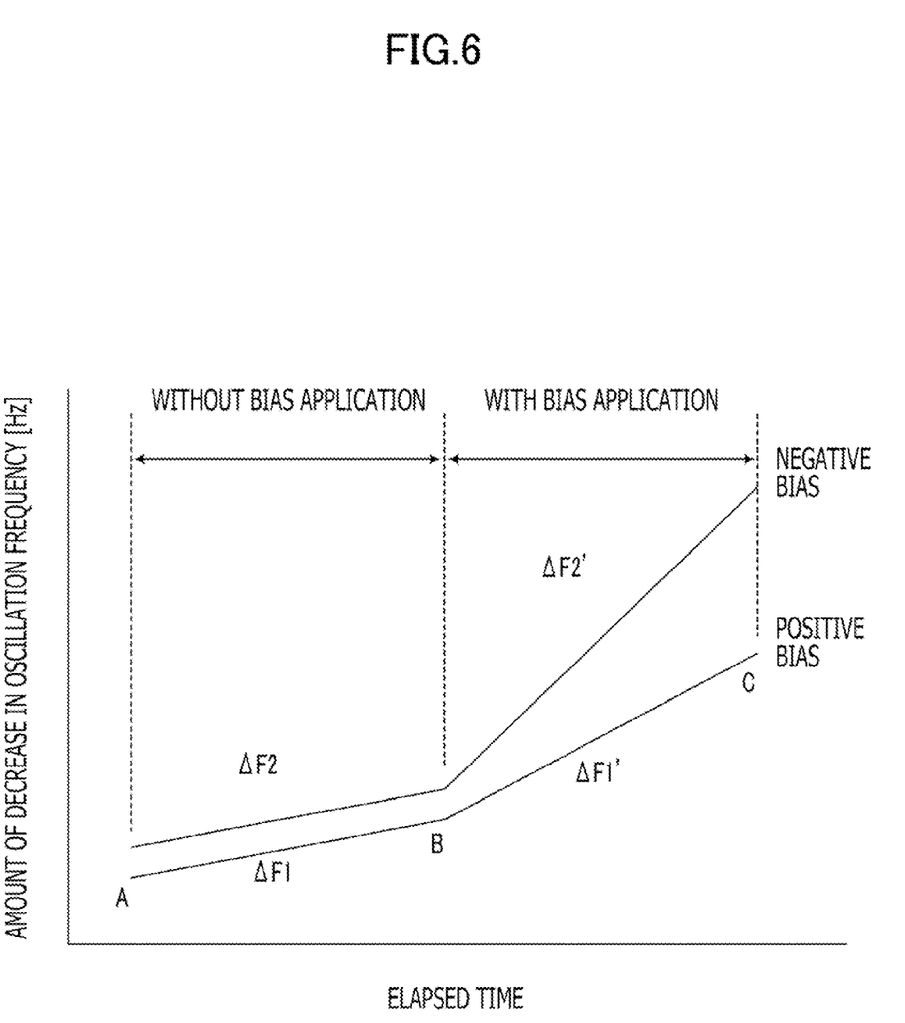
FIG. 6 is a graph illustrating an example of an analyzing method using the ion analyzing apparatus according to the second embodiment.

FIG. 6 is a graph illustrating an analyzing method using the ion analyzing apparatus according to the second embodiment. The method is described in conjunction with FIG. 5.

Firstly, the storage controller 37 sends a control signal B1 to the switching circuit 35, the positive bias generating circuit 33, and the negative bias generating circuit 34. After the switching circuit 35, the positive bias generating circuit 33, and the negative bias generating circuit 34 receive the control signal B1, changes in ΔF1 and ΔF2 in the respective oscillation frequencies are measured without application of voltages to the first sensor 23 and the second sensor 24 from elapsed time A to B, such as for ten minutes. Here, with the use of the switching circuit 35, the first oscillation circuit 26 or the second oscillation circuit 27 to be coupled to the frequency measuring circuit 36 is switched periodically, such as every second, and the oscillation frequencies of the first oscillation circuit 26 and the second oscillation circuit 27 are alternately measured. Gradients ΔF1 and ΔF2 from A to B, which are obtained by the measurements, are values that reflect the amount of adsorption per unit time, without application of voltages, of the first sensor 23 and the second sensor 24, respectively.

Changes in the frequencies of the first sensor 23 and the second sensor 24 may be measured at the same time by alternately measuring the oscillation frequencies of the first oscillation circuit 26 and the second oscillation circuit 27.

Then, the storage controller 37 sends a control signal B2 to the switching circuit 12. After the switching circuit 12 receives the control signal B2, changes in ΔF1' and ΔF2' in the frequencies are measured with application of a positive bias to the first sensor 23 and a negative bias to the second sensor 24 from elapsed time B to C, such as for ten minutes. The absolute values of the applied positive bias and the applied negative bias are, for example, about 100 V. With the use of the switching circuit 35, the first oscillation circuit 26 or the second oscillation circuit 27 to be coupled to the frequency measuring circuit 36 is switched every second, for example, and the oscillation frequencies of the first oscillation circuit 26 and the second oscillation circuit 27 are alternately measured.

Since the first sensor 23 is charged positively upon application of the positive bias to the first sensor 23, negative ions are adsorbed on the first sensor 23. In contrast, since the second sensor 24 is charged negatively upon application of the negative bias to the second sensor 24, positive ions are adsorbed on the second sensor 24.

Matter adsorbed on the first sensor 23 as a result of application of the positive bias and matter adsorbed on the second sensor 24 as a result of application of the negative bias include matter with electric charge and matter without electric charge. The effects of the matter without electric charge may be removed by comparing changes in the oscillation frequencies, which are measured without application of voltages, with changes in the oscillation frequencies, which are measured with application of the biases.

The gradient of a difference between $\Delta F1$, which is measured without application of a voltage, and $\Delta F1'$, which is measured with application of the positive bias, is a value that reflects the density of the negative ions. The gradient of a difference between $\Delta F2$, which is measured without application of a voltage, and $\Delta F2'$, which is measured with application of the negative bias, is a value that reflects the density of the positive ions.

As described above, the density of the negative ions and the density of the positive ions may be measured at the same time by alternately measuring the oscillation frequencies of the first oscillation circuit 26 and the second oscillation circuit 27.

With a comparison of the gradient of the difference between $\Delta F1$ and $\Delta F1'$ with the gradient of the difference between $\Delta F2$ and $\Delta F2'$, the positive-negative balance of ions in the space where the measurements have been done may be detected, and an ionizer's effect of discharging a target to be discharged may be estimated. Changes in the ion densities in time may be constantly measured (monitored) by repeating the foregoing procedure.

Figure 7:
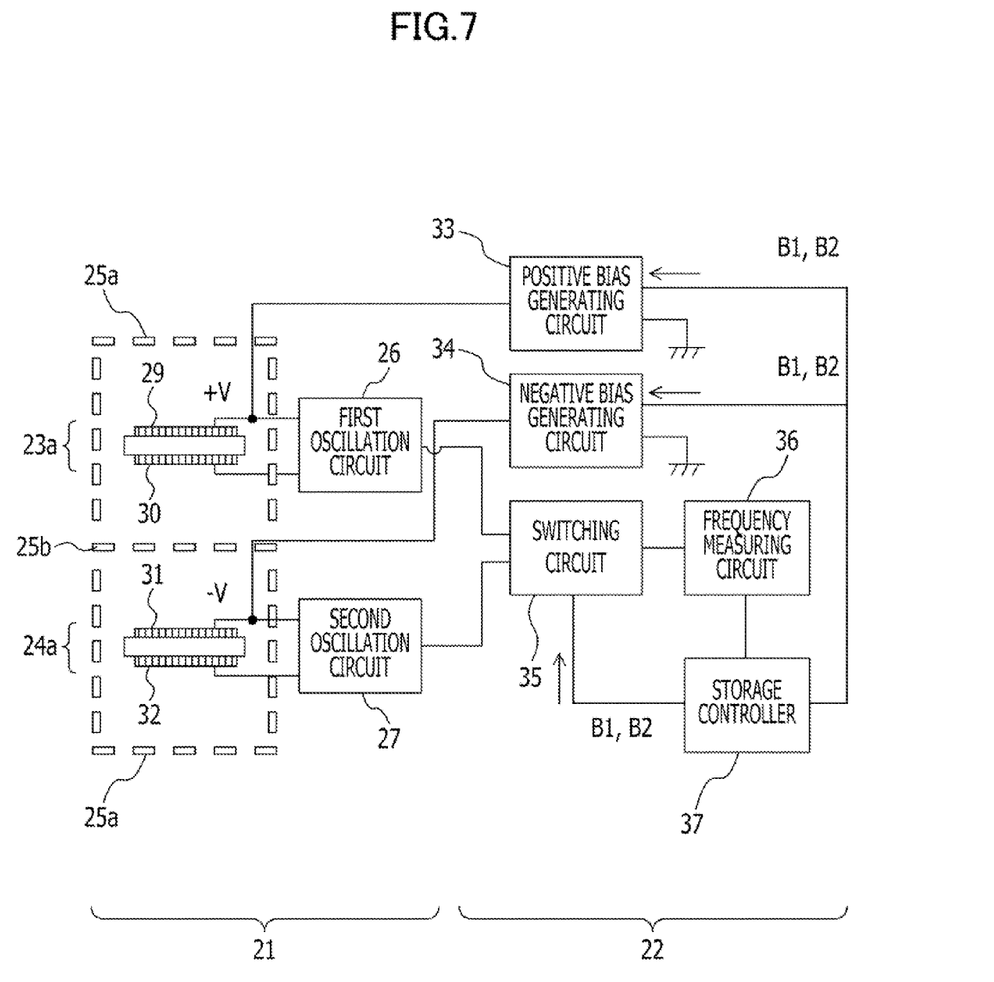
FIG. 7 is a diagram illustrating another example of the ion analyzing apparatus according to the second embodiment.

FIG. 7 is a diagram illustrating another example of the ion analyzing apparatus according to the second embodiment.

As illustrated in FIG. 7, a counter electrode 25b is provided between a first sensor 23a and a second sensor 24a. The first sensor 23a and the second sensor 24a are individually substantially surrounded by a counter electrode 25a and the counter electrode 25b.

A reduction in the amount of adsorption involved in a chemical reaction between positive and negative ions may be reduced when the first sensor 23a and the second sensor 24a are individually substantially surrounded by the counter electrode 25a and the counter electrode 25b. Blocking of adsorption of ions due to an electric field generated between the first sensor 23a and the second sensor 24a may also be reduced.

Figure 8:
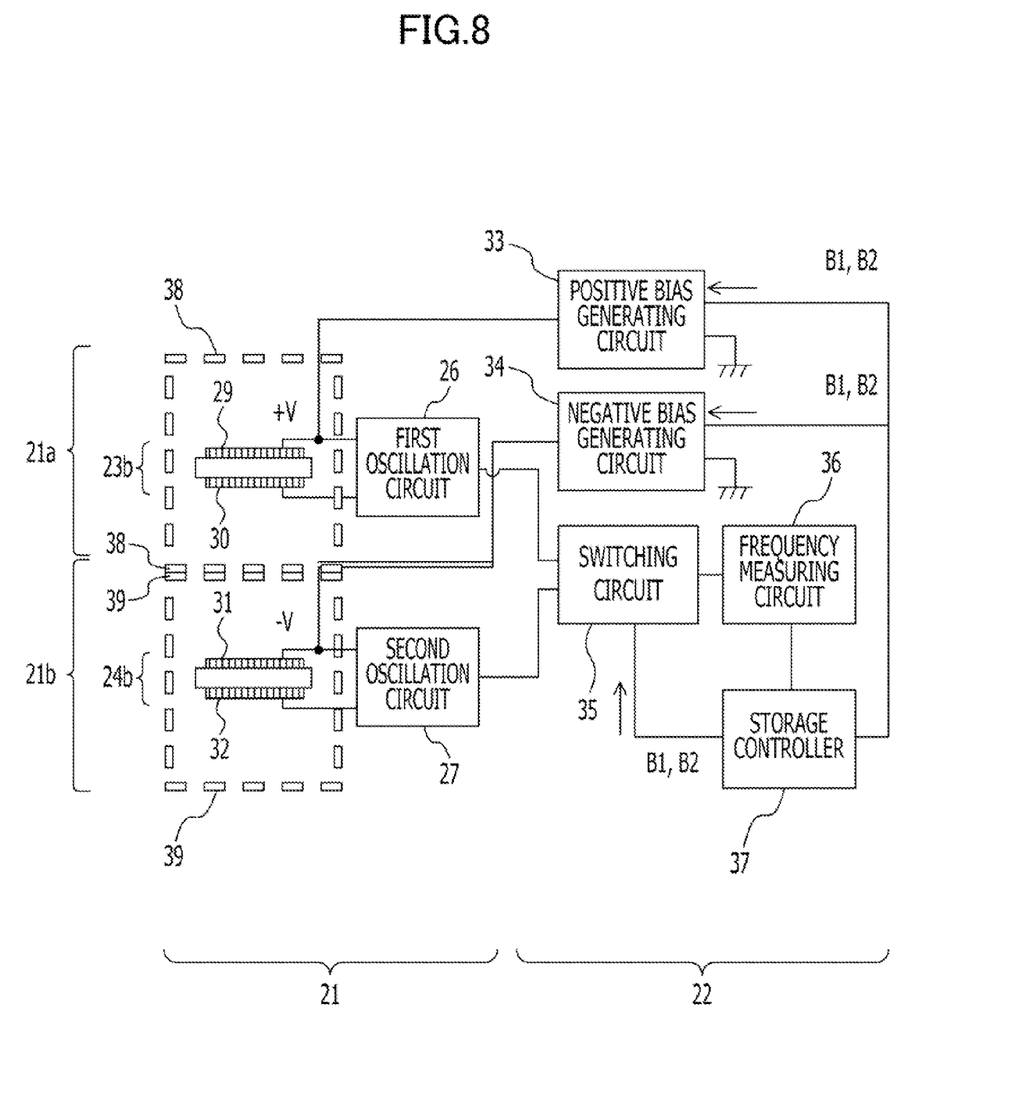
FIG. 8 is a diagram illustrating another example of the ion analyzing apparatus according to the second embodiment.

FIG. 8 is a diagram illustrating another example of the ion analyzing apparatus according to the second embodiment.

As illustrated in FIG. 8, a sensor unit 21a including a first counter electrode 38 positioned so as to substantially surround a first sensor 23b may be joined, e.g., back to back, with a sensor unit 21b including a second counter electrode 39 positioned so as to substantially surround a second sensor 24b.

According to the foregoing configuration, because the sensor unit 21 of the ion analyzing apparatus may be manufactured by joining the two sensor units 21a and 21b which have undergone a manufacturing process and a test process and been determined to be non-defective units, the manufacturing yields of the sensor unit 21 may be improved.

Figure 9:
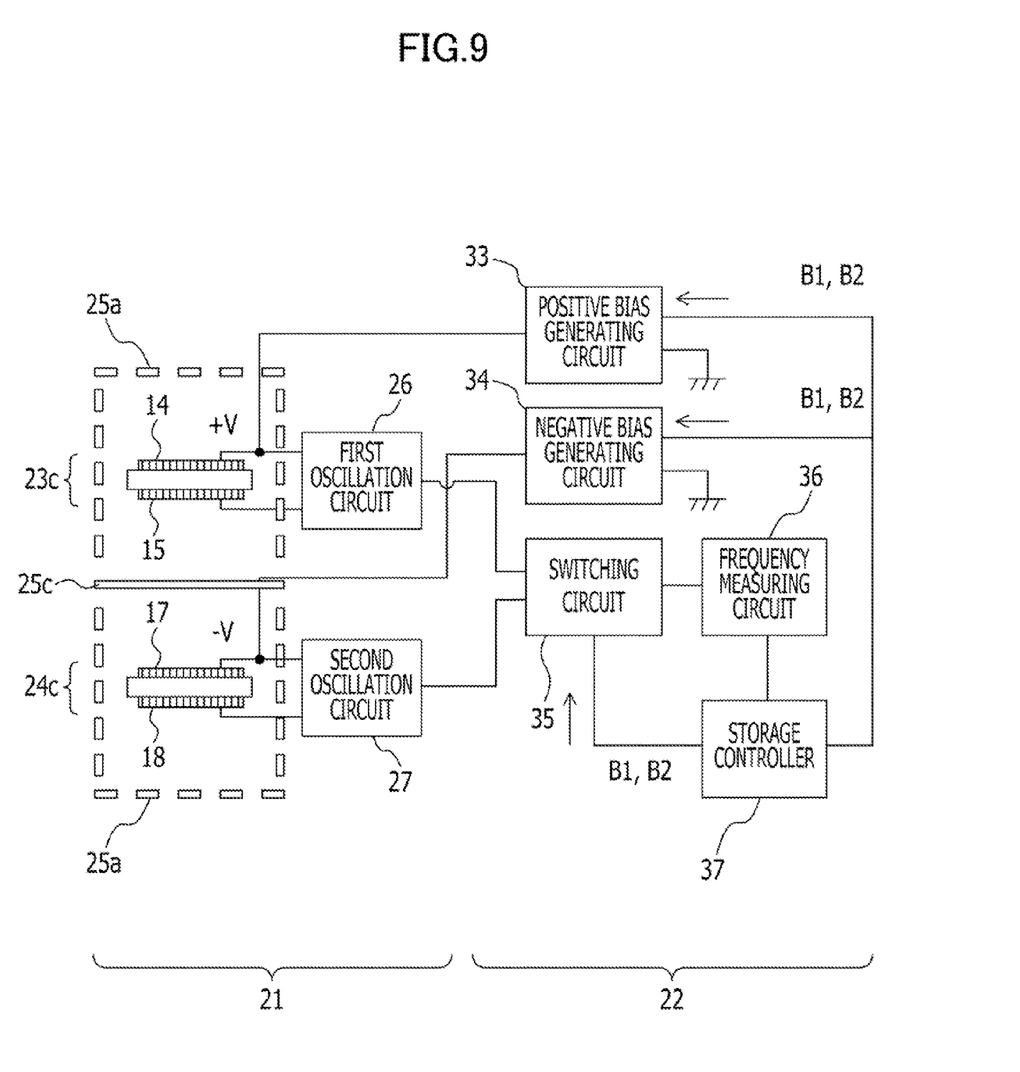
FIG. 9 is a diagram illustrating another example (part 2) of the ion analyzing apparatus according to the second embodiment.

FIG. 9 is a diagram illustrating another example (part 2) of the ion analyzing apparatus according to the second embodiment.

As illustrated in FIG. 9, a flat plate with a smaller aperture ratio than that of the counter electrode 25a is used as a counter electrode 25c provided between a first sensor 23c and a second sensor 24c.

According to the foregoing configuration, because mutual movement of ions between the first sensor 23c and the second sensor 24c is less likely to occur, the counter electrode 25c has a higher effect of suppressing a change in the distribution of ions around the first sensor 23c and the second sensor 24c.

A third embodiment will now be described with reference to FIGS. 10 and 11.

Figure 10:
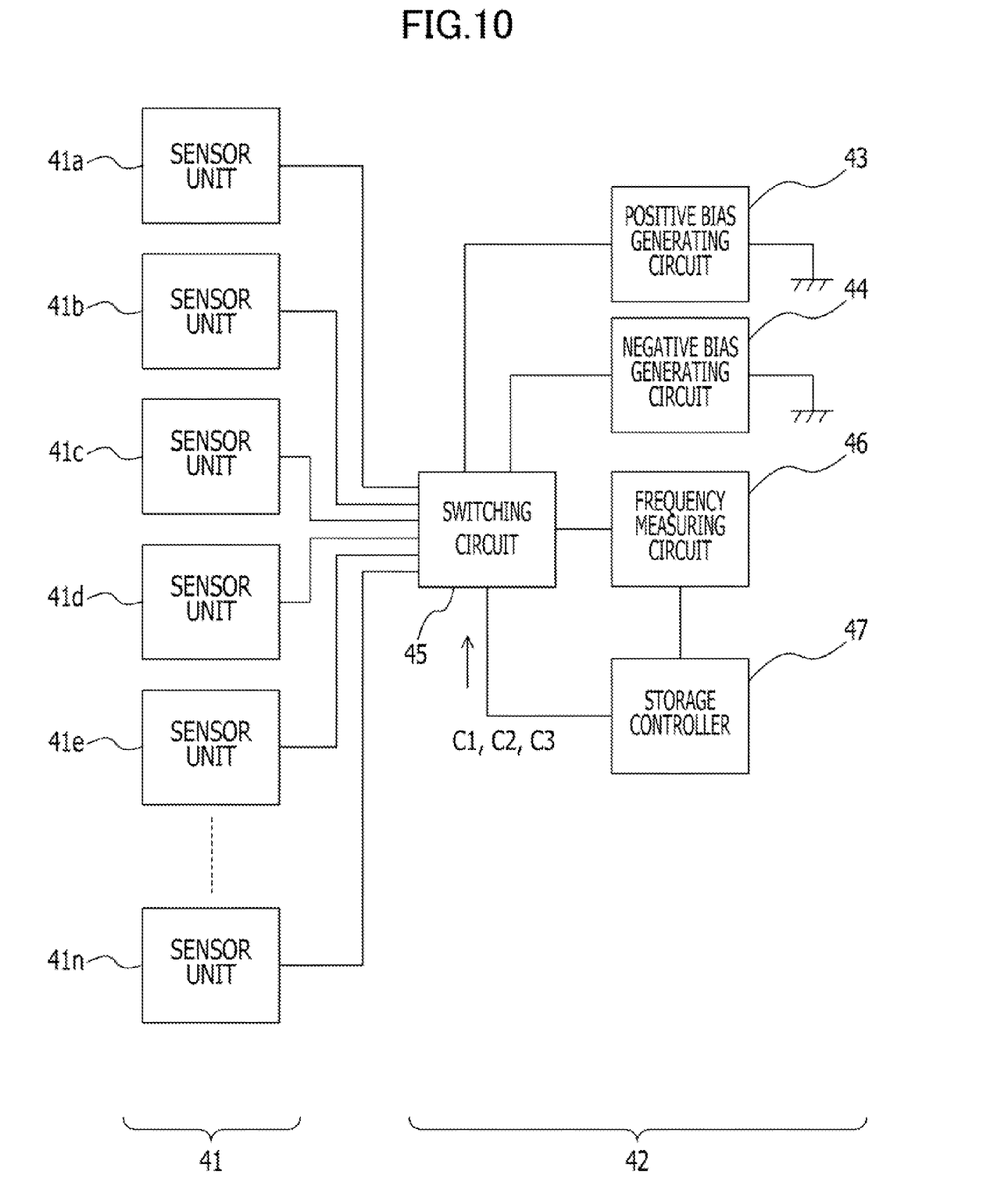
FIG. 10 is a diagram illustrating an exemplary ion analyzing apparatus according to a third embodiment.

FIG. 10 is a diagram illustrating an ion analyzing apparatus according to the third embodiment.

The ion analyzing apparatus includes a sensor unit group 41 including a plurality of sensor units 41a to 41n, and a control unit 42.

Each unit of the ion analyzing apparatus will now be described in more detail.

Each sensor unit of the sensor unit group 41 includes a sensor including a quartz crystal oscillator, a counter electrode having openings that is positioned so as to substantially surround the sensor, and an oscillation circuit (none of them are illustrated in the drawings). For example, the sensor unit 1 shown in FIG. 1 in the first embodiment or the sensor unit 21 shown in FIG. 5 in the second embodiment may be used as each sensor unit.

The control unit 42 includes a positive bias generating circuit 43, a negative bias generating circuit 44, a switching circuit 45, a frequency measuring circuit 46, and a storage controller 47.

Each sensor unit 41a to 41n is coupled to the common switching circuit 45. The positive bias generating circuit 43 and the negative bias generating circuit 44 are independently coupled to the switching circuit 45. The switching circuit 45 is also coupled to the frequency measuring circuit 46. The frequency measuring circuit 46 is coupled to the storage controller 47. The storage controller 47 may store the value of a change in the frequency of the oscillation circuit of each sensor unit, which is measured by the frequency measuring circuit 46.

Further, the storage controller 47 drives the positive bias generating circuit 43 and the negative bias generating circuit 44 by sending a control signal C1 to the switching circuit 45, and performs control for applying a positive or negative bias to the sensor unit group 41 and for switching connection of each sensor unit with the frequency measuring circuit 46 by using the switching circuit 45. For example, a PC may be used as the storage controller 47.

According to the foregoing configuration, measurements of ion densities may be performed at many points by using the plurality of sensor units 41a to 41n, and the ion distribution in space from an ionizer to a target to be discharged may be detected with a high accuracy. Since measurements at many points using one control unit may be performed by connecting the sensor units to the switching circuit 45 one at a time, the size and cost of the ion analyzing apparatus may be reduced.

Next, an analyzing method using the ion analyzing apparatus according to the third embodiment will be described with reference to FIG. 10.

Firstly, the storage controller 47 sends the control signal C1 to the switching circuit 45. After the switching circuit 45 receives the control signal C1, changes $\Delta Fa$ to $\Delta Fn$ (hereinafter called $\Delta F$) in the oscillation frequencies of the respective sensor units are measured one at a time by the frequency measuring circuit 46 without application of a voltage to the sensor units, while the sensor unit to be coupled to the switching circuit 45 is sequentially switched.

Then, the storage controller 47 sends a control signal C2 to the switching circuit 45. After the switching circuit 45 receives the control signal C2, changes ΔFa' to ΔFn' (hereinafter called ΔF') in the oscillation frequencies of the respective sensor units are sequentially measured by the frequency measuring circuit 46 with application of a positive bias to the sensor units one at a time, while the sensor unit to be coupled to the switching circuit 45 is switched one at a time.

Since the sensor units are charged positively upon application of the positive bias to the sensor units, negative ions are adsorbed on the sensor units. The gradient of a difference obtained by subtracting ΔF, which is measured without application of a voltage, from ΔF', which is measured with application of the positive bias, is a value that reflects the density of the negative ions. That is, the tendency of the density distribution of the negative ions at each measurement point may be detected.

Then, the storage controller 47 sends a control signal C3 to the switching circuit 45. After the switching circuit 45 receives the control signal C3, changes ΔFa" to ΔFn" (hereinafter called ΔF") in the frequencies of the respective sensor units are sequentially measured by the frequency measuring circuit 46 with application of a negative bias to the sensor units one at a time, while the sensor unit to be coupled to the switching circuit 45 is sequentially switched.

Since the sensor units are charged negatively upon application of the negative bias to the sensor units, positive ions are adsorbed on the sensor units. The gradient of a difference obtained by subtracting ΔFa, which is measured without application of a voltage, from ΔFa", which is measured with application of the negative bias, is a value that reflects the density of the positive ions at an arbitrary measurement point. The tendency of the density distribution of the positive ions at each measurement point may be detected by obtaining the gradient of the difference at each measurement point by using the foregoing method.

With a comparison of ΔF' and ΔF", which are measured using the foregoing method, the positive-negative balance of ion densities at the individual measurement points may be detected, and an ionizer's effect of discharging a target to be discharged may be detected. Changes in the ion densities in time may be substantially constantly measured (monitored) by repeating the foregoing procedure.

Figure 11:
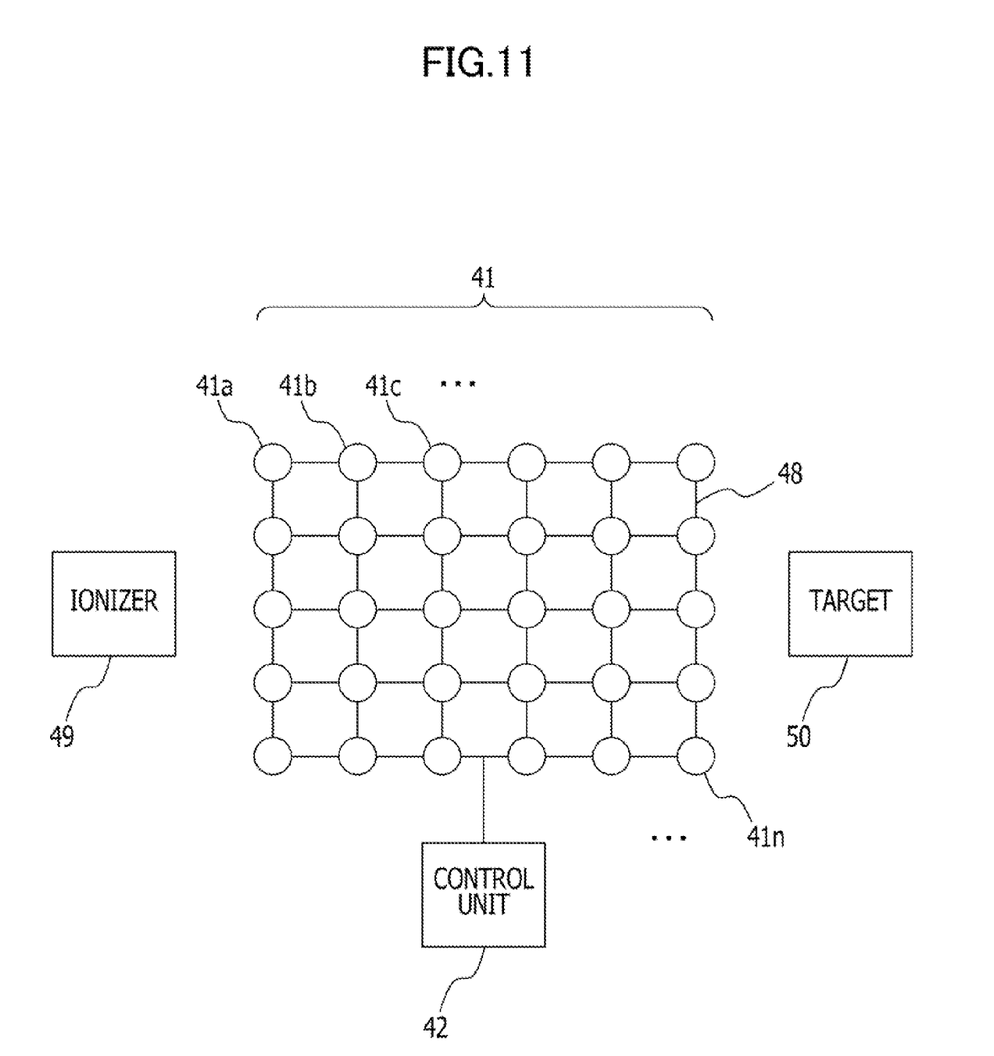
FIG. 11 is a diagram illustrating an example of the arrangement of sensor units of the ion analyzing apparatus according to the third embodiment.

FIG. 11 is a diagram illustrating an example of the arrangement of sensor units of the ion analyzing apparatus according to the third embodiment.

As illustrated in FIG. 11, the plurality of sensor units 41a to 41n of the sensor unit group 41 are arranged in a matrix in space from an ionizer 49 to a target 50 to be discharged. Adjacent sensor units are coupled to each other via a wire 48. For example, a method of suspending the sensor units downward may be used when the sensor units are to be arranged in three dimensions.

The control unit 42 sequentially switches a sensor unit to be connected periodically, such as every second, by using a method such as specifying the matrix coordinates, and the control unit 42 measures, one at a time, the oscillation frequencies of the oscillation circuits of the individual sensor units. With this method, the ion densities of each sensor unit may be measured. The ion analyzing apparatus according to the present invention may also be used when, besides the third embodiment, the positive-negative ion distribution in space where no ionizer is provided is to be detected.

What is claimed is:

1. An ion analyzing apparatus comprising:
    a first sensor;
    a second sensor;
    at least one counter electrode having openings, the at least one counter electrode being positioned so as to substantially surround the first sensor and the second sensor;
    a positive bias generating circuit coupled to the first sensor; and
    a negative bias generating circuit coupled to the second sensor;
    each of the first sensor and the second sensor includes a quartz crystal and a pair of electrodes positioned on surfaces of the quartz crystal;
    one of the pair of electrodes of the first sensor is coupled to the positive bias generating circuit, and one of the pair of electrodes of the second sensor is coupled to the negative bias generating circuit;
    a first oscillation circuit coupled to the pair of electrodes of the first sensor;
    a second oscillation circuit coupled to the pair of electrodes of the second sensor; and
    a frequency measuring circuit configured to measure a change in frequency of the first oscillation circuit or the second oscillation circuit.

2. The ion analyzing apparatus of claim 1, wherein the counter electrode has a mesh shape.

3. The ion analyzing apparatus of claim 1, wherein the first sensor and the second sensor are individually substantially surrounded by the at least one counter electrode.

4. The ion analyzing apparatus of claim 1, wherein the frequency measuring circuit is coupled via a switching circuit to the first oscillation circuit and the second oscillation circuit.

5. The ion analyzing apparatus of claim 1, wherein:
    the at least one counter electrode includes first and second counter electrodes, each having openings;
    the first sensor is substantially surrounded by the first counter electrode; and
    the second sensor is substantially surrounded by the second counter electrode.

\* \* \* \* \*